United States Patent
Irwin et al.

(10) Patent No.: US 11,712,353 B2
(45) Date of Patent: Aug. 1, 2023

(54) EXPANSION MEMBERS FOR IMPLANTABLE DEVICES AND ASSOCIATED SYSTEMS AND METHODS

(71) Applicant: W. L. Gore & Associates, Inc., Newark, DE (US)

(72) Inventors: Craig W. Irwin, Parks, AZ (US); James D. Silverman, Flagstaff, AZ (US); Tyson J. Skelton, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 17/052,259

(22) PCT Filed: Apr. 30, 2019

(86) PCT No.: PCT/US2019/029976
§ 371 (c)(1),
(2) Date: Nov. 2, 2020

(87) PCT Pub. No.: WO2019/213120
PCT Pub. Date: Nov. 7, 2019

(65) Prior Publication Data
US 2021/0052404 A1    Feb. 25, 2021

Related U.S. Application Data

(60) Provisional application No. 62/665,695, filed on May 2, 2018.

(51) Int. Cl.
*A61F 2/915*    (2013.01)
*A61F 2/82*    (2013.01)
*A61F 2/89*    (2013.01)

(52) U.S. Cl.
CPC ............... *A61F 2/915* (2013.01); *A61F 2/82* (2013.01); *A61F 2/89* (2013.01); *A61F 2250/0063* (2013.01)

(58) Field of Classification Search
CPC .... A61F 2/07; A61F 2/82; A61F 2/844; A61F 2/915; A61F 2/86; A61F 2/89; A61F 2250/0063
See application file for complete search history.

(56) References Cited

U.S. PATENT DOCUMENTS

| | | | |
|---|---|---|---|
| 4,973,189 A | 11/1990 | Bechtold | |
| 5,522,881 A | 6/1996 | Lentz | |

(Continued)

FOREIGN PATENT DOCUMENTS

| | | |
|---|---|---|
| EP | 1779809 A1 | 5/2007 |
| EP | 2151217 A1 | 2/2010 |

(Continued)

OTHER PUBLICATIONS

International Preliminary Report on Patentability received for PCT Patent Application No. PCT/US2010/051974, dated Apr. 19, 2012, 10 pages.

(Continued)

*Primary Examiner* — Dinah Baria

(57) ABSTRACT

A medical device frame including an undulating frame element defining a series of peaks each defining a longitudinal splay angle, circumferential cant angle, or combinations thereof. In some examples, the series of peaks are non-overlapping when the frame is in an expanded configuration and overlap when the frame is in the collapsed configuration. The longitudinal splay angle and/or circumferential cant angle may remain relatively unchanged between the expanded and collapsed configurations (e.g., within about 15%).

14 Claims, 9 Drawing Sheets

(56) References Cited

U.S. PATENT DOCUMENTS

| | | |
|---|---|---|
| 6,042,605 A | 3/2000 | Martin et al. |
| 6,911,040 B2 | 6/2005 | Johnson et al. |
| 7,637,939 B2 | 12/2009 | Tischler |
| 7,704,275 B2 | 4/2010 | Schmid et al. |
| 7,846,195 B2 | 12/2010 | Berra et al. |
| 7,918,884 B2 | 4/2011 | Majercak et al. |
| 7,951,188 B2 | 5/2011 | Ainsworth et al. |
| 8,480,725 B2 | 7/2013 | Rasmussen et al. |
| 9,629,735 B2 | 4/2017 | Zukowski |
| 2001/0020181 A1 | 9/2001 | Layne |
| 2001/0049554 A1 | 12/2001 | Ruiz et al. |
| 2005/0154448 A1 | 7/2005 | Cully et al. |
| 2006/0155364 A1 | 7/2006 | Holloway et al. |
| 2006/0195172 A1 | 8/2006 | Luo et al. |
| 2006/0259123 A1 | 11/2006 | Dorn |
| 2007/0142902 A1 | 6/2007 | Yadin |
| 2007/0208413 A1 | 9/2007 | Nakano |
| 2008/0009932 A1 | 1/2008 | Ta et al. |
| 2008/0023103 A1 | 1/2008 | Ballinger |
| 2008/0039926 A1 | 2/2008 | Majercak et al. |
| 2008/0103589 A1 | 5/2008 | Cheng et al. |
| 2009/0048663 A1 | 2/2009 | Greenberg |
| 2009/0163996 A1 | 6/2009 | Bregulla |
| 2009/0210049 A1 | 8/2009 | Thielen et al. |
| 2009/0306763 A1 | 12/2009 | Roeder et al. |
| 2010/0234932 A1 | 9/2010 | Arbefeuille et al. |
| 2010/0286760 A1 | 11/2010 | Beach et al. |
| 2011/0144736 A1 | 6/2011 | Prabhu et al. |
| 2011/0144737 A1 | 6/2011 | Burgermeister et al. |
| 2011/0144738 A1 | 6/2011 | Casey |
| 2011/0213455 A1 | 9/2011 | Obradovic et al. |
| 2012/0330402 A1 | 12/2012 | Vad et al. |
| 2013/0197657 A1 | 8/2013 | Anca et al. |
| 2014/0142684 A1 | 5/2014 | Zukowski |
| 2017/0181874 A1 | 6/2017 | Zukowski |
| 2020/0229951 A1 | 7/2020 | Zukowski |

FOREIGN PATENT DOCUMENTS

| | | |
|---|---|---|
| JP | 2002-536057 A | 10/2002 |
| JP | 2003-245359 A | 9/2003 |
| JP | 2007-506493 A | 3/2007 |
| JP | 2009-131397 A | 6/2009 |
| JP | 2011-508625 A | 3/2011 |
| JP | 2012-520153 A | 9/2012 |
| JP | 2012-524641 A | 10/2012 |
| JP | 2013-507194 A | 3/2013 |
| WO | 98/51186 A1 | 11/1998 |
| WO | 01/06952 A1 | 2/2001 |
| WO | 2004/047687 A1 | 6/2004 |
| WO | 2005/016793 A1 | 2/2005 |
| WO | 2008/130572 A1 | 10/2008 |
| WO | 2009/082444 A1 | 7/2009 |
| WO | 2010/105195 A2 | 9/2010 |
| WO | 2011/044459 A2 | 4/2011 |
| WO | 2012/092627 A1 | 7/2012 |

OTHER PUBLICATIONS

International Preliminary Report on Patentability received for PCT Patent Application No. PCT/US2013/070132, dated May 28, 2015, 8 pages.

International Search Report and Written Opinion received for PCT Patent Application No. PCT/US2010/051974, dated Apr. 4, 2011, 14 pages.

International Search Report and Written Opinion received for PCT Patent Application No. PCT/US2019/029976, dated Jul. 1, 2019, 12 pages.

International Search Report for PCT/US2013/070132 dated Feb. 6, 2014, corresponding to U.S. Appl. No. 14/079,353, 5 pages.

International Written Opinion received for PCT Patent Application No. PCT/US2013/070132, dated Feb. 6, 2014, 6 pages.

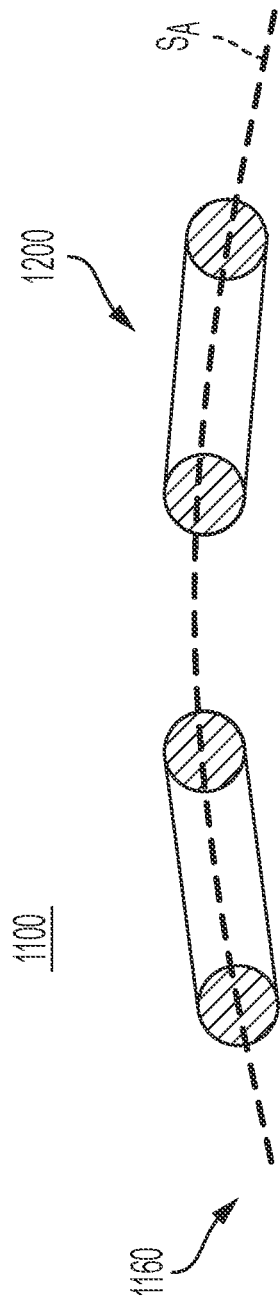
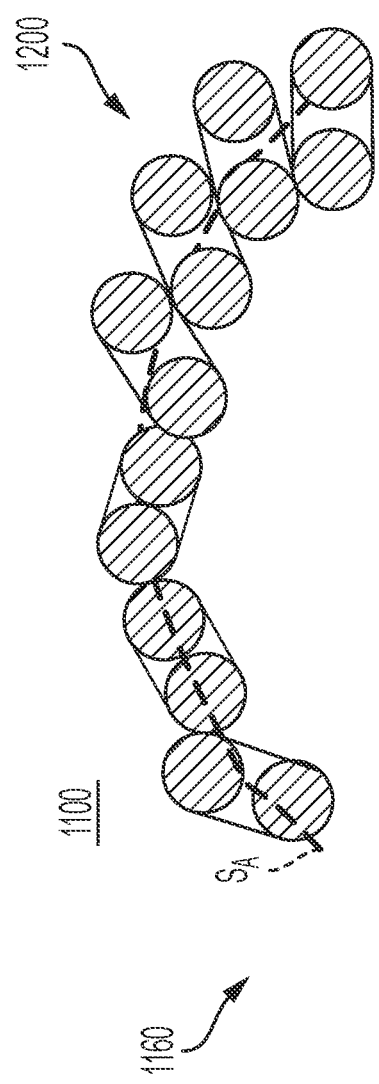

EXPANSION MEMBERS FOR IMPLANTABLE DEVICES AND ASSOCIATED SYSTEMS AND METHODS

CROSS-REFERENCE TO RELATED APPLICATION

This application is a U.S. 371 application of International Application PCT/US2019/029976, filed Apr. 30, 2019, which claims the benefit of Provisional Application No. 62/665,695, filed May 2, 2018, which are incorporated herein by reference in their entireties for all purposes.

FIELD

The present disclosure generally relates to expansion members for implantable medical devices. More specifically, the disclosure relates to expansion members with radially offset portions for improved shingling and/or nesting.

BACKGROUND

Various types of implantable medical devices have a frame that is expandable from a collapsed, delivery state to an enlarged deployed state, including expandable stents, filters, prosthetic valves, and others. Stents and stent grafts are often used to open or support a lumen of an anatomic vessel or duct. In many procedures, it is desirable to compress an expandable, implantable medical device into a compacted, or compressed state before delivering the device to a desired treatment location in the lumen at which it is expanded, either via self-expansion, expansion under an internal force (e.g., balloon expansion), combinations thereof, or via another mechanism.

SUMMARY

Various examples relate to implantable medical devices having a frame that is expandable. In particular, various examples relate to a frame having expansion members with radially offset portions for improved shingling and/or nesting.

According to one example ("Example 1"), a medical device has an expanded configuration and a collapsed configuration. The medical device includes a frame having a central longitudinal axis extending in a longitudinal direction, a first end, a second end, a lumen extending between the first end and the second end, and a length. The frame also includes an undulating from element along its length. The frame element includes a first series of peaks oriented toward the first end and a second series of peaks oriented toward the second end. The first series of peaks defines a first average apex angle and the second series of peaks defines a second average apex angle that is less than the first average apex angle.

According to another example ("Example 2") further to Example 1, each of the first series of peaks is angled radially outward relative to the central longitudinal axis at a first longitudinal splay angle.

According to another example ("Example 3") further to any one of Examples 1 to 2, the first series of peaks are radially offset relative to the second series of peaks.

According to another example ("Example 4") further to any one of Examples 1 to 3, each peak of the first series of peaks includes a first leg portion and a second leg portion. There is a first apex angle between the first and second leg portions. The first apex angle of each peak of the first series of peaks collectively defines the first average apex angle. Each peak of the second series of peaks also includes a first leg portion and a second leg portion and a second apex angle between the first and second leg portions of the second series of peaks. The second apex angle of each peak of the second series of peaks collectively define the second average apex angle.

According to another example ("Example 5") further to any one of Examples 1 to 4, the second average apex angle is less than the first average apex angle when the frame is in the expanded configuration and when the frame is in the collapsed configuration.

According to another example ("Example 6") further to any one of Examples 1 to 5, the frame defines a first diameter corresponding to the first series of peaks and the frame defines a second diameter corresponding to the second series of peaks. The second diameter is less than the first diameter.

According to another example ("Example 7") further to Example 6, the second diameter is less than the first diameter when the frame is in the expanded configuration and when the frame is in the collapsed configuration.

According to another example ("Example 8") further to any one of Examples 1 to 7, the frame includes a first circumferential row defining the first and second series of peaks. The frame also includes a second circumferential row including a first series of peaks and a second series of peaks. The first series of peaks of the first row overlap with the second series of peaks of the second row when the frame is in the collapsed configuration. The first series of peaks of the first row are non-overlapping with the second series of peaks of the second row when the frame is in the expanded configuration.

According to another example ("Example 9"), a medical device has an expanded configuration and a collapsed configuration. The medical device includes a frame having a central longitudinal axis, a circumferential direction that is transverse to the central longitudinal axis, a first end, a second end, a lumen extending between the first end and the second end, and a length. The frame also includes an undulating frame element along its length. The frame element includes a first series of peaks oriented toward the first end and a second series of peaks oriented toward the second end. The first series of peaks is circumferentially canted at a first cant angle.

According to another example ("Example 10") further to Example 9, each of the second series of peaks is circumferentially canted at a second cant angle.

According to another example ("Example 11") further to Example 10, the first cant angle is equal to the second cant angle.

According to another example ("Example 12") further to any of Examples 9 to 11, the frame includes a first circumferential row defining the first and second series of peaks. The frame also includes a second circumferential row including a first series of peaks and a second series of peaks. The first series of peaks of the first row overlap with the second series of peaks of the second row when the frame is in the collapsed configuration. The first series of peaks of the first row are non-overlapping with the second series of peaks of the second row when the frame is in the expanded configuration.

According to another example ("Example 13") further to any of Examples 9 to 12, the first series of peaks are non-overlapping with the second series of peaks when the frame is in the expanded configuration. The first series of peaks overlap with the second series of peaks when the frame is in the collapsed configuration.

According to another example ("Example 14") further to Example 13, the first cant angle remains within 15% of its value between the collapsed configuration and the expanded configuration.

According to another example ("Example 15") a medical device has an expanded configuration and a collapsed configuration. The medical device includes a frame having a central longitudinal axis, a circumferential direction that is transverse to the central longitudinal axis, a first end, a second end, a lumen extending between the first end and the second end, and a length. The frame includes an undulating frame element along its length. The frame element includes a first series of peaks oriented toward the first end and a second series of peaks oriented toward the second end. Each of the first series of peaks is longitudinally splayed radially outward at a first splay angle.

According to another example ("Example 16") further to Example 15, the frame includes a first circumferential row defining the first and second series of peaks. The frame also includes a second circumferential row including a first series of peaks and a second series of peaks. The first series of peaks of the first row overlap with the second series of peaks of the second row when the frame is in the collapsed configuration. The first series of peaks of the first row are non-overlapping with the second series of peaks of the second row when the frame is in the expanded configuration.

According to another example ("Example 17") further to Example 16, the first splay angle remains within 15% of its value between the collapsed configuration and the expanded configuration.

According to another example ("Example 18") a method of making the medical device of any one of Examples 1 to 17 includes imparting a circumferential cant and/or a longitudinal splay to the first series of peaks.

According to another example ("Example 19") a method of making the medical device of any one of Examples 1 to 18 includes transitioning the frame from the collapsed configuration, in which the frame includes a plurality of overlapping peaks, and the expanded configuration, in which the frame is characterized by an absence of overlapping peaks.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 4A is a transverse cross-section of a prior art device in an expanded configuration, according to some embodiments.

FIG. 4B is a transverse cross-section of a prior art device in a compressed configuration, according to some embodiments.

The accompanying drawings are included to provide a further understanding of the disclosure and are incorporated in and constitute a part of this specification, illustrate embodiments, and together with the description serve to explain the principles of the disclosure.

DETAILED DESCRIPTION

Various embodiments relate to designs for frames of expandable (e.g., self-expanding or balloon expandable) devices, such as stents, stent grafts, filters, and prosthetic valves, among others. Aspects of this disclosure relate to controlled frame compression profiles, where uncontrolled compression profiles can result in random or otherwise uncontrolled deformation in areas of the frame design. For example, various portions of the frame may overlap or abut one another in a random, or otherwise variable or uncontrolled manner, resulting in increased stresses and strains. Irregular or non-uniform stress and strain distributions in the frame design may result in a reduction in reliability and/or increase in variability of the compression ratio achievable by a particular device design. In various examples, designs according to the instant disclosure include a pre-set angular offset in the stent apices, such as a circumferential and/or longitudinal splay or deflection, to facilitate improved nesting and/or shingling of the frame with itself and to help distribute stresses when the frame is in the compressed or collapsed configuration.

Figure 1:
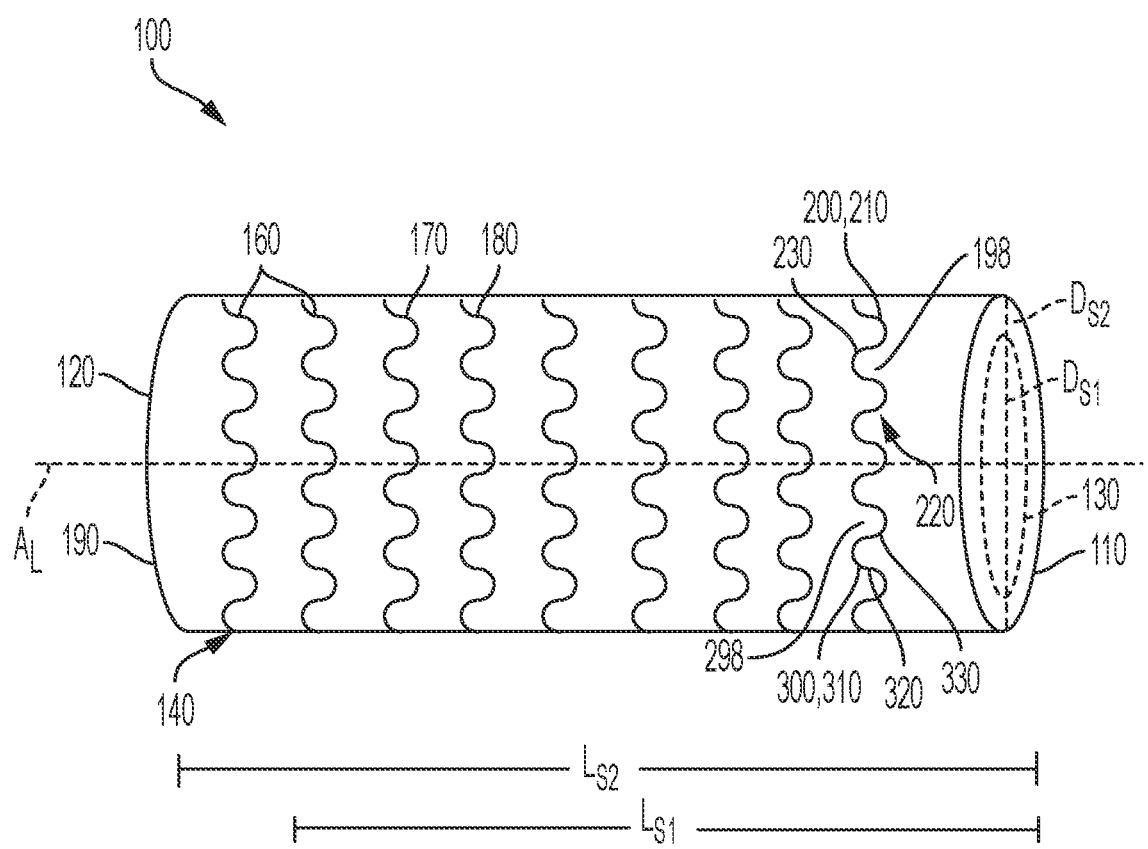
FIG. 1 is a schematic view of a medical device in the form of a stent-graft, according to some embodiments.

FIG. 1 is a schematic view of an expandable frame 100 of an implantable medical device (e.g., a stent graft as shown) having a central longitudinal axis $A_L$, a first end 110, a second end 120, and a lumen 130 extending between the first end 110 and the second end 120. The frame 100 includes at least one frame element 140 along the length. In some examples, the frame element 140 is of an undulating or sinusoidal design, an angular, or zig-zag design, has a constant, regular, repeating pattern, or has another configuration as desired. The frame element 140 may be helically formed as a series of interconnected turns or rows, or formed as a plurality of separate, discrete rings or rows by a plurality of frame elements similar to the frame element 140, for example.

As shown generally in FIG. 1, the frame element 140 defines one or more circumferential rows 160, which may also be described as one or more turns, or passes around the circumference of the frame 100. The frame element 140 may include a plurality of circumferential rows 160 as shown in FIG. 1. The circumferential rows 160 include a first row 170 and a second row 180. As mentioned above, the frame element 140 may be continuous or include a number of discrete rows. In instances where the frame element 140 is continuous, the frame element 140 may extend continuously to form one or more longitudinally-adjacent rows 160. For example, the frame element 140 optionally extends continuously from the first end 110 to the second end 120 of the frame 100 to define each of the circumferential rows 160 that are continuous with one another (e.g., first row 170 and second row 180 are continuous with one another). In some examples, the frame element 140 extends continuously in a helical pattern to form the rows 160. In instances where the frame element 140 is discontinuous, the frame element 140 may be discontinuous at one or more locations between, for example, the first end 110 and the second end 120 of the frame 100, such that one or more adjacent rows 160 (e.g., first row 170 and second row 180) are discrete, or disconnected from one another. For example, one or more of the rows 160 are optionally formed as a discrete ring, or turn, around the circumference of the frame 100.

In some embodiments, the frame 100 is diametrically compressible or, in other terms, radially compressible, to a compressed configuration having a compressed, or undeployed diameter $D_{S1}$. The frame 100 is generally compressible from an expanded, or deployed configuration having an expanded, or deployed diameter $D_{S2}$. In some examples, the frame 100 is longitudinally compressible along longitudinal axis $A_L$ to a compressed, or undeployed configuration having a compressed, or undeployed length $L_{S1}$ from an expanded, or deployed configuration having an expanded length, or deployed length $L_{S2}$. In various embodiments, the frame 100 is both longitudinally compressible and diametrically compressible to a compressed configuration having the compressed, or undeployed diameter $D_{S1}$ and length $L_{S1}$ from an expanded, or deployed configuration having the expanded diameter, or deployed diameter $D_{S2}$ and length $L_{S2}$.

The frame 100 is also configured to be expandable from the compressed configuration to the expanded configuration. For example, the frame 100 is expandable to the expanded configuration having the expanded, or deployed diameter $D_{S2}$ and length $L_{S2}$ from the compressed configuration. In some embodiments, the frame 100 may be self-expanding (e.g., being formed of an elastically deformable material, such as NiTi alloy), radially expandable via application of an internal expansion force (e.g., using a balloon catheter), or combinations thereof. The term "expandable" is inclusive of self-expansion, expansion by force, and combinations thereof. Although the frame 100 is shown in the form of a stent attached to a tubular graft member 190, the frame 100 and associated principles of operation are optionally employed with a variety of other expandable, implantable medical devices, including implantable filters, occluders, anastomosis devices, prosthetic valves, and others.

In some embodiments, the frame element 140 is formed by winding one or more wires, cutting, etching, or otherwise formed. The frame element 140 is optionally formed of metals/alloys (e.g., stainless steel or a shape memory materials such as nitinol) or non-metallic materials (e.g., biocompatible polymeric materials). Various biocompatible polymeric materials may include, for example, polytetrafluoroethylene (ePTFE), polyester, polyurethane, fluoropolymers, such as perfluoroelastomers and the like, polytetrafluoroethylene, silicones, urethanes, ultra-high molecular weight polyethylene, and aramid fibers, among others.

The frame element 140 includes a first series of peaks 200 oriented toward the first end 110 and a second series of peaks 300 oriented toward the second end 120. In some examples (e.g., where the frame element 140 is sinusoidal in shape) each of the first series of peaks 200 and second series of peaks 300 are separated by inflection points defining the undulating pattern of the frame element 140 as discussed above.

Figure 2:
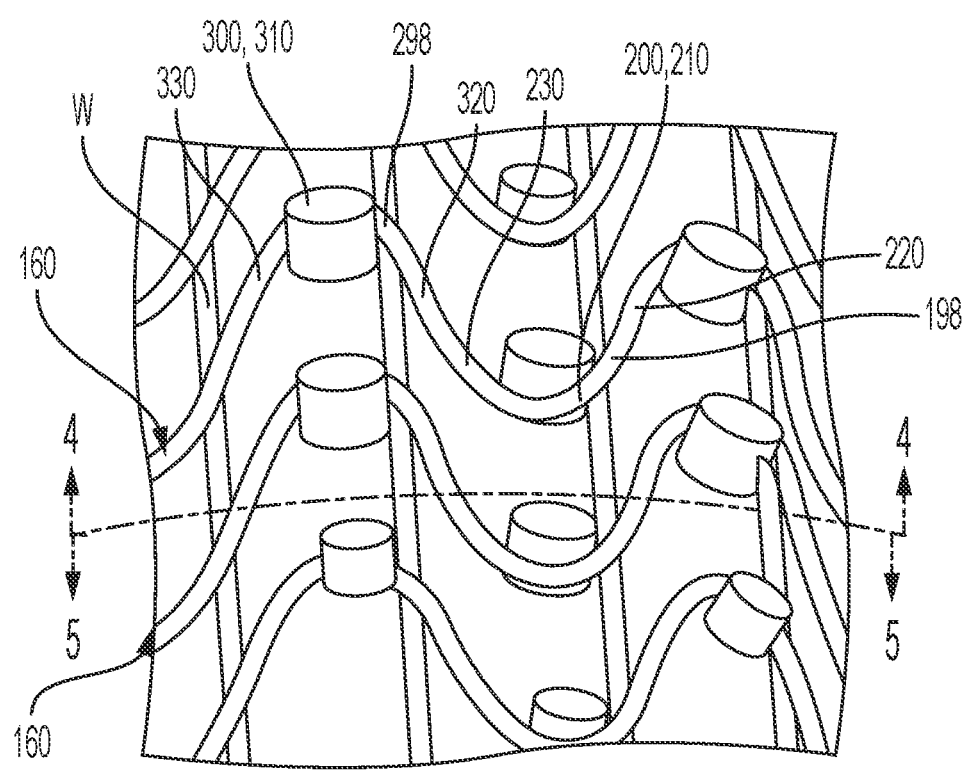
FIG. 2 shows a portion of an implantable medical device having rows of frame elements, according to some embodiments.

FIG. 2 shows a portion of an implantable medical device 100 including rows 160 of frame elements 140, according to some embodiments. As shown, a first series of peaks 200 is oriented toward the first end 110 of the frame 100 and a second series of peaks 300 is oriented toward the second end 120 of the frame 100. Each peak of the first series of peaks 200 has an apex 210, a first leg 220, and a second leg 230, each of the first leg 220 and the second leg 230 extending from the apex 210. The first leg 220 and the second leg 230 of each apex 210 of the first series of peaks 200 meet to form a first apex angle $A_1$. Each of the first apex angles $A_1$ of the first series of peaks 200 collectively define a first average apex angle calculated by averaging the apex angles $A_1$ of each peak of the first series of peaks 200. The term "apex" includes both relatively curved and relatively sharp apices. The first apex angle $A_1$ can be measured in plane with the first and second legs 220, 230. For examples, the first apex angle $A_1$ can be measured between the first leg 220 and the second leg 230 or, in other terms, from the first leg 220 to the second leg 230.

Similar to the first series of peaks 200, each of the second series of peaks 300 also has an apex 310, and a first leg 320 and a second leg 330 extending from the apex 310. The first leg 320 and the second leg 330 of each apex 310 meet to form a second apex angle $A_2$. The second apex angle $A_2$ of each of the second series of peaks 300 define a second average apex angle calculated by averaging the apex angles of each peak of the second series of peaks 300. The second apex angle $A_2$ can similarly be measured between the first leg 320 and the second leg 330 or, in other terms, from the first leg 320 to the second leg 330.

As shown in FIG. 2, the first leg 320 of each of the second series of peaks 300 extends from a corresponding second leg 230 of the first series of peaks 200, the first leg 320 transitioning to the second leg 230 around an inflection point, or mid-point between the first leg 320 and the second leg 230. Similarly, the second leg 330 of each of the second series of peaks 300 extends from a corresponding first leg 220 of the first series of peaks 200, the second leg 330 transitioning to the first leg 220 around an inflection point, or mid-point between the second leg 330 and the first leg 220.

Figure 3A:
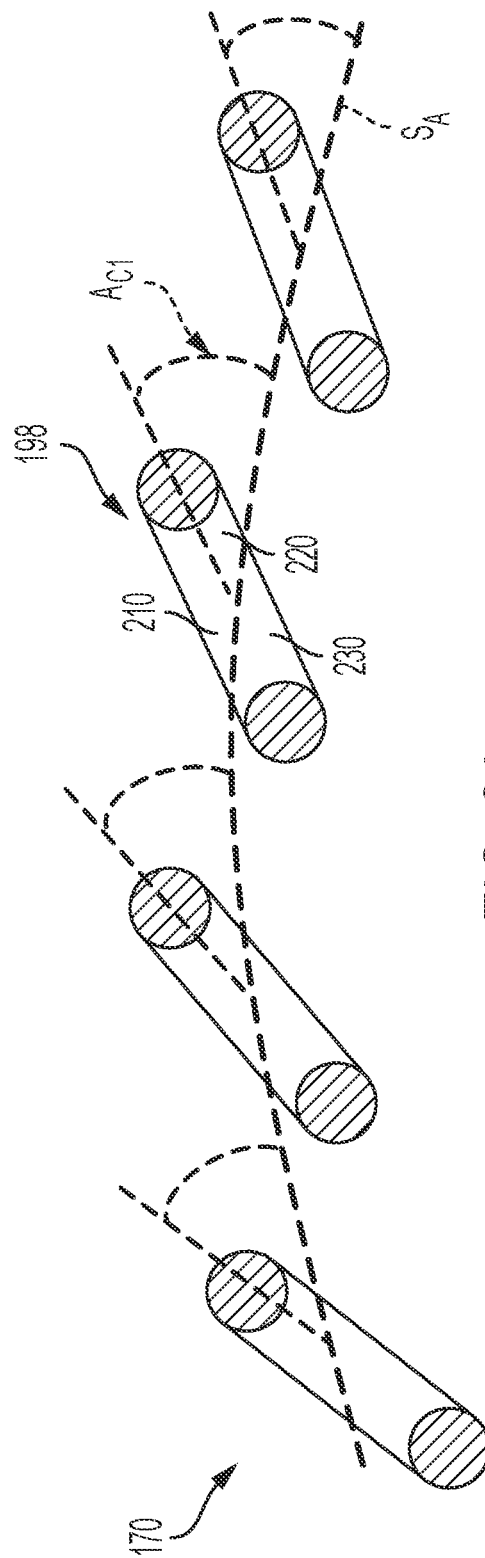
FIG. 3A shows a first transverse cross-section of the frame of FIG. 2 in an expanded configuration and FIG. 3C shows a second transverse cross-section of the frame of FIG. 2 in the expanded configuration, according to some embodiments.
Figure 3B:
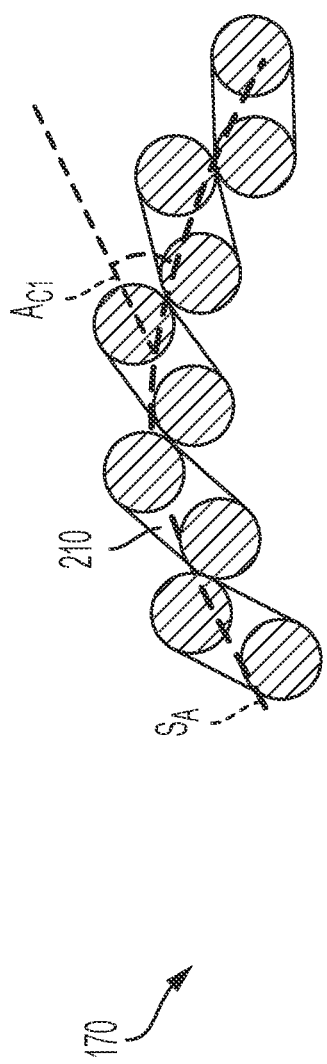
FIG. 3B shows a first transverse cross-section of the frame of FIG. 2 in a compressed configuration and FIG. 3D shows a second transverse cross-section of the frame of FIG. 2 in the compressed configuration, according to some embodiments.

FIGS. 3A and 3B show a transverse cross-section of the frame 100 along line 4-4 of FIG. 2. FIG. 3A shows the frame 100 in the expanded configuration and FIG. 3B shows the frame 100 in the collapsed configuration. FIGS. 3A and 3B show the first row 170, according to some embodiments, with each of the other rows 160 of the frame element 140 being similarly configured. FIG. 3A is oriented along line 4-4 of FIG. 2 and shows the first series of peaks 200, and in particular the first and second legs 220 and 230 extending from the apices 210 while the stent 100 is in an expanded or deployed configuration. In some embodiments, one or more peaks (e.g., each peak or every other peak) of the first series of peaks 200 is canted, pitched, or otherwise angled and includes a raised portion 198 located adjacent to and/or laterally offset from the apex 210 of the peak. As shown, the first series of peaks 200 are each angled radially outward, with one side higher than the other, such that the first series of peaks 200 are canted relative to the average circumference $S_A$ of the frame 100. The first series of peaks 200 are each canted relative to a tangent line of the average circumference taken at each of the apices 210 to form a first cant angle $A_{C1}$. In different terms, one side of the peak is raised relative to the other side of the peak, or one leg (e.g., the first leg 220) is radially, or outwardly raised relative to the other leg (e.g., the second leg 230) so that one or more peaks of the first series of peaks 200 is canted, pitched, or otherwise angled. For reference, the term "laterally offset" can also be described as circumferentially offset or located to the side of a particular feature.

Figure 3C:
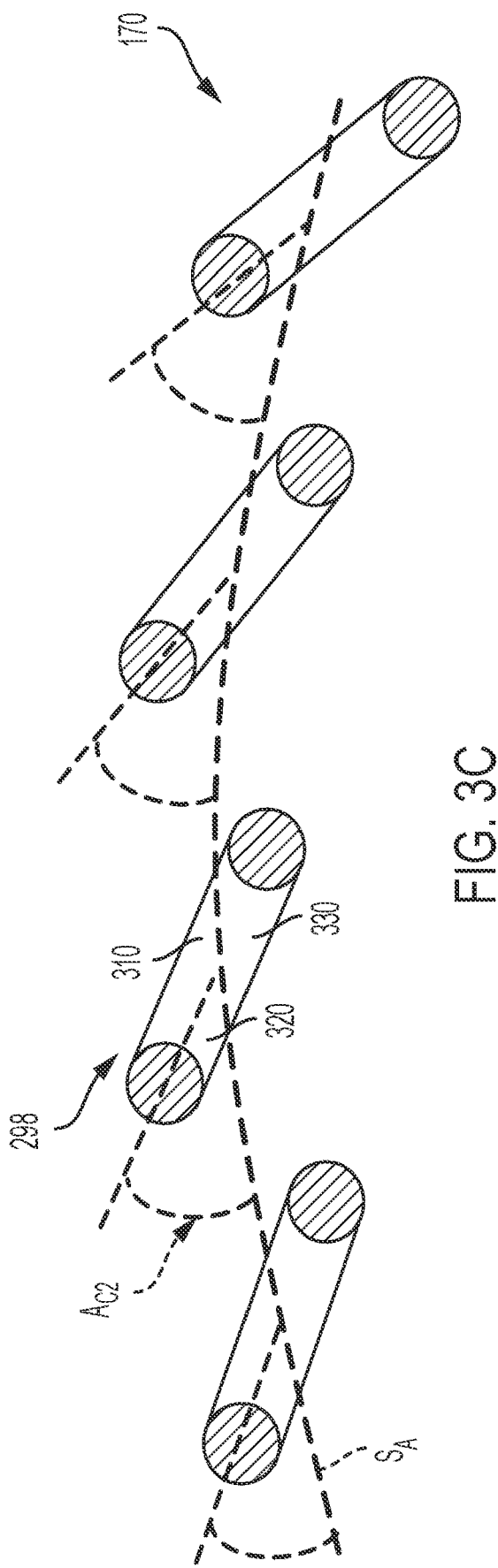
Figure 3D:
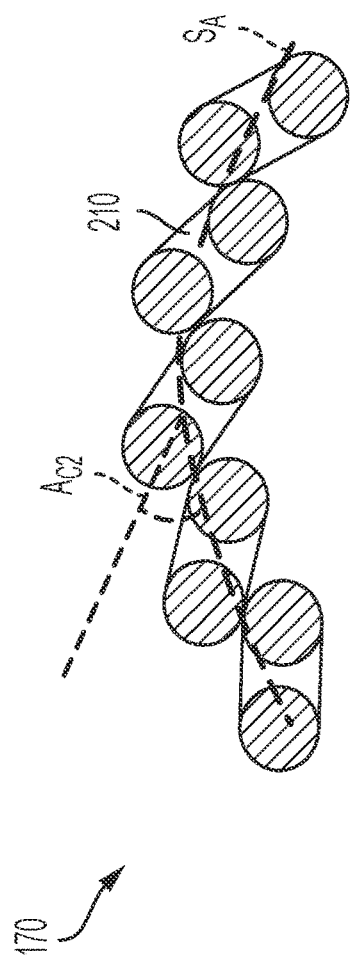

FIGS. 3C and 3D show a transverse cross-section of the frame 100 along line 5-5 of FIG. 2. FIG. 3C shows the frame 100 in the expanded configuration and FIG. 3D shows the frame in the compressed configuration. As shown in FIG. 3C, in some embodiments, one or more peaks (e.g., each peak or every other peak) of the second series of peaks 300 is also canted, pitched, or otherwise angled and includes a raised portion 298 located adjacent to and/or laterally offset from the apex 310 of the peak. The second series of peaks 300 are each canted relative to a tangent line of the average circumference taken at each of the apices 310 to form a second cant angle $A_{C2}$. In different terms, one side of the peak is raised relative to the other side of the peak, or one leg (e.g., the first leg 320) is radially, or outwardly raised relative to the other leg (e.g., the second leg 330) so that one or more peaks of the second series of peaks 300 is canted, pitched, or otherwise angled. As shown in the compressed configuration of FIG. 3B, the second series of peaks 300 remains angled radially outward from the average outer surface $S_A$ of the frame 100 such that the apices 310 overlap or shingle adjacent portions of the row 170. In some embodiments, the second cant angle $A_{C2}$ of each apex 310 while the frame 100 is in the compressed configuration remains approximately equal to the second cant angle $A_{C2}$ while the frame is in the expanded configuration.

According to various embodiments, one or more rows 160 (e.g., the first row 170, the second row 180, all rows, or some portion of the total number of rows 160) includes oppositely-facing peaks that have one side raised outwardly relative to the other side (e.g., similar to the first and second series of peaks 200, 300 as previously described) to define a plurality of circumferentially-canted, or circumferentially-angled apices. In different terms, the frame element 140 defines one or more circumferential rows 160, each of which includes a plurality of first apices oriented in a first longitudinal direction (e.g., toward the first end) that are circumferentially canted at a first cant angle $A_{C1}$ with respect to a tangent line of the average circumference taken at each of the apices 210, and a plurality of second apices oriented in a second longitudinal direction (e.g., toward the second end) that are circumferentially-canted at a second cant angle Ace with respect to a tangent line of the average circumference taken at each of the apices 310. In some examples, the first cant angle $A_{C1}$ and second cant angle Ace are the same, although different cant angles are contemplated. As will be further described, inclusion of cant angle features can help facilitate compacting of the device into a reduced diametric profile. For example, the first series of peaks 200 do not overlap the second series of peaks 300 when the frame 100 is in the expanded configuration, however, the first series of peaks 200 are configured to overlap the second series of peaks 300 when the frame 100 is in the collapsed configuration to facilitate compacting of the device as well as reduce the amount of stress and strain on the frame 100.

For reference, the term circumferentially-canted generally refers to the apices being canted, pitched or otherwise angled about the circumference of the frame 100. The angle, pitch, or cant of the first series of peaks 200 and second series of peaks 300 can optionally be determined relative to a tangent line taken along the average circumference of the frame 100 at the apices 210, 310 of each of the series of peaks 200, 300 of each of the rows 160, as discussed above.

FIG. 3B is oriented along line 4-4 of FIG. 2 and shows the first series of peaks 200, and in particular the first and second legs 220 and 230 extending from the apices 210 while the stent 100 is in a collapsed configuration. As shown, the first series of peaks 200 remains angled radially outward from the average outer surface $S_A$ of the frame 100 such that the apices 210 overlap or shingle adjacent portions of the row 170. For reference, the term "shingle" or "shingling" may be lateral overlapping of adjacent legs or lateral overlapping of adjacent frame portions of the row 170 or, in some examples, later overlapping of adjacent peaks. In some embodiments, such shingling may promote a more even distribution of stress and strain along the frame 100. In some embodiments, the first cant angle $A_{C1}$ of each apex 210 while the frame 100 is in the compressed configuration remains approximately equal to the first cant angle $A_{C1}$ of each apex 210 while the frame 100 is in the expanded configuration. For example, the first cant angle $A_{C1}$ may remain within about 5%, 10%, 15%, or, in some embodiments, more than 15% of its value between the collapsed configuration and the expanded configuration.

In some embodiments, the frame 100 includes a first row 170 and a second row 180 (FIG. 1), where each of the first row 170 and second row 180 include a first series of peaks 200 and a second series of peaks 300. In some embodiments, the first row 170 and second row 180 do not overlap when the frame 100 is in the expanded configuration. In other words, the first series of peaks 200 of the first row 170 and the second series of peaks 300 of the second row 180 do not overlap when the frame 100 is in the expanded configuration. In some embodiments, the first row 170 and the second row 180 may overlap when the frame 100 is in the collapsed configuration or, in other words, the first series of peaks 200 of the first row 170 may overlap the second series of peaks 300 of the second row 180 when the frame 100 is in the collapsed configuration, thereby facilitating shingling and promoting a more even distribution of stress and/or strain along the frame 100.

For comparison, FIG. 4A is an example of a transverse cross-section of a first row 1160 of a frame 1100 without canting in an expanded state. Only two of the first series of peaks 1200 is shown in FIG. 4A. As shown, the first series of peaks 1200 is not angularly offset relative to tangent and generally follows the average circumference of the frame 1100.

FIG. 4B shows the frame 1100 of FIG. 4A without canting in a compacted state. As shown in FIG. 4B, when the frame 1100 is compacted, there is a potential for the first series of peaks 1200 to arrange themselves in a non-uniform manner, giving rise to increased and/or irregular strains for some of the peaks 1200 and potentially a less desirable packing ratio (e.g., the frame 1100 is not able to be compacted to the same extent as it would be with a more regular stacking and arrangement of peaks 1200).

In some embodiments, the raised portions 198 and/or 298 are raised or angled radially outward an amount equal to the diameter of one frame member 140 to promote shingling over adjacent portions of the frame member 140. This may be done, for example, by wrapping each row 160 of the frame member 140 around a mandrel having longitudinally oriented lengths of wire W disposed thereon, as shown in FIG. 2. In some embodiments, the wire W may have a diameter equal to that of the frame member 140. As shown, each portion of the row 160 overlying the wire W will be raised by approximately the diameter of the wire W, thereby imparting a circumferential cant to the first series of peaks 200 and/or the second series of peaks 300 and forming a desired first cant angle $A_{C1}$ and/or second cant angle $A_{C2}$.

The diameter of the wire W and/or frame member 140 may vary depending on the deployed diameter $D_{S1}$ of the frame 100. For example, a frame 100 with a larger deployed diameter $D_{S1}$ may have a larger diameter frame member 140 and vice versa. In various examples, the average deployed diameter $D_{S1}$ of the frame 100 may be about 5 mm, 6 mm, 7 mm, 8 mm, or greater than 8 mm such as, for example, from 8 mm to 13 mm. In one example, a frame with an average deployed diameter $D_{S1}$ of about 8 mm has a frame member 140 with a diameter from 0.2 mm to 0.3 mm. Thus, in such an example, each of the first series of peaks 200 would be raised from about 0.2 mm to 0.3 mm relative to the average outer surface $S_A$ of the frame 100, though other arrangements and configurations are also possible.

Though FIG. 3B shows every leg of the first series of peaks 200 as angled radially outward to form raised portions 198, other arrangements and configurations are also contemplated herein. For example, as discussed above, in some embodiments, every other leg may be angled radially outward (e.g., there may be a raised portion 198 adjacent to every other peak of the first series of peaks 200) or other select portions of the stent member 140 may be angled radially outward as desired. In different terms, the raised portions 198 may be substantially uniform or evenly spaced along the row 170 and/or frame 100, or may be unevenly spaced in a variety of combinations or patterns as desired.

Though not shown in FIGS. 3A-B, as discussed above for the first series of peaks 200, the second series of peaks 300 can also be angled radially outward, with one side higher than the other, such that the first series of peaks 200 are canted relative to the average circumference $S_A$ of the frame 100 (e.g., canted relative to a tangent line of the average circumference taken at each of the apices 310) and form a second cant angle $A_{C2}$. Similarly, upon compression, the angled, canted, or raised portions 298 overlap or shingle adjacent, non-canted portions of the frame member 140. Similar to the first cant angle $A_{C1}$, the second cant angle $A_{C2}$ of the second apex 310 while the frame 100 is in the compressed configuration may remain approximately equal to the second cant angle Ace of the second apex 310 while the frame 100 is in the expanded configuration. For example, the second cant angle $A_{C2}$ may remain within about 5% of its value between the collapsed configuration and the expanded configuration.

Figure 5:
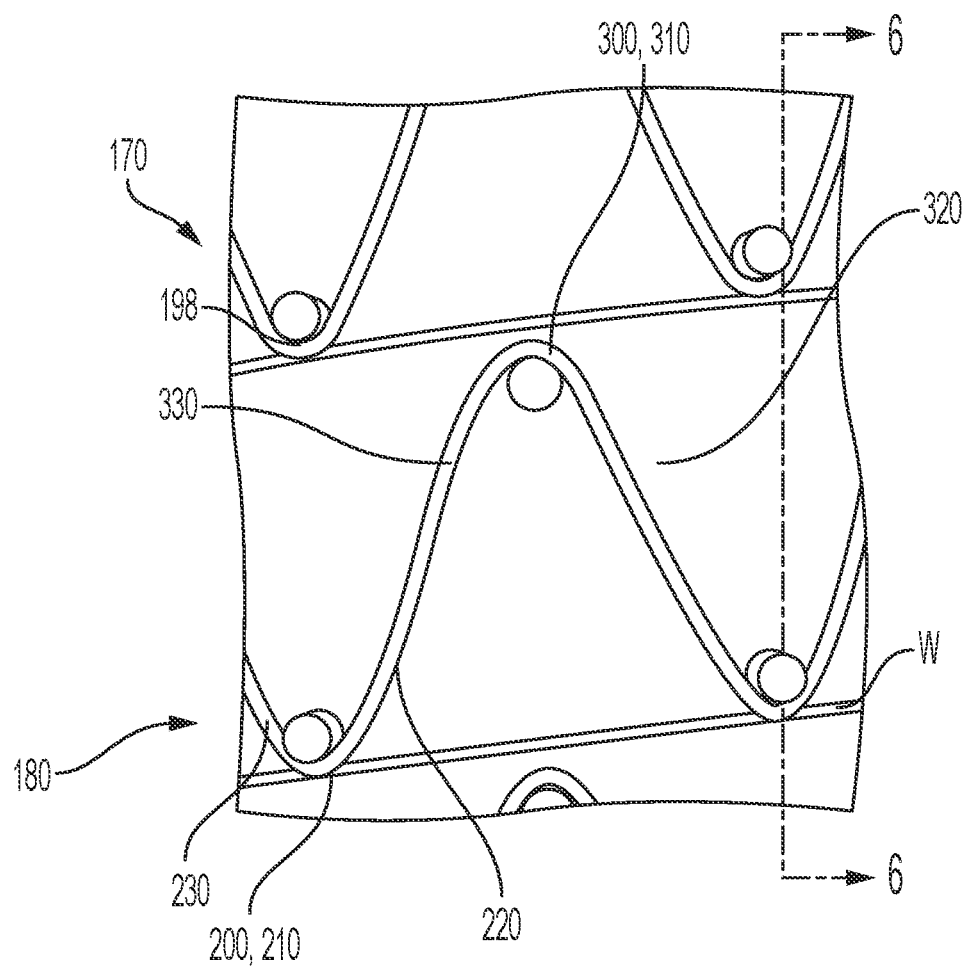
FIG. 5 shows a portion of an implantable medical device having rows of frame elements, according to some embodiments.

FIG. 5 shows another example frame 100, according to some embodiments. As discussed above, each row 160 includes a first series of peaks 200 oriented toward the first end 110 of the frame 100 and a second series of peaks 300 oriented toward the second end 120 of the frame 100. Each of the first series of peaks 200 has a first leg 220 and a second leg 230. The first leg 220 and the second leg 230 form a first apex 210, the two legs angularly offset to define a first apex angle $A_1$. The apex angles of each of first series of peaks 200 define a first average apex angle calculated by averaging the first apex angles $A_1$ of each of the first series of peaks 200. Each of the second series of peaks 300 also has a first leg 320 and a second leg 330, the first leg 320 and second leg 330 forming a second apex 310 and angularly offset to define a second apex angle $A_2$. The apex angles of each of the second series of peaks 300 define a second average apex angle calculated by averaging the second apex angles $A_2$ of each of the second series of peaks 300.

In some embodiments, one or more peaks of the first series of peaks 200 (e.g., each peak or every other peak) includes a raised portion 198 located at the apex 210 of each of the first series of peaks 200. In other words, each of the first series of peaks 200 is longitudinally splayed, tilted, slanted, or otherwise angled radially outward relative to the central longitudinal axis $A_L$ of the frame 100 to form a first splay angle $A_{S1}$.

Figure 6A:
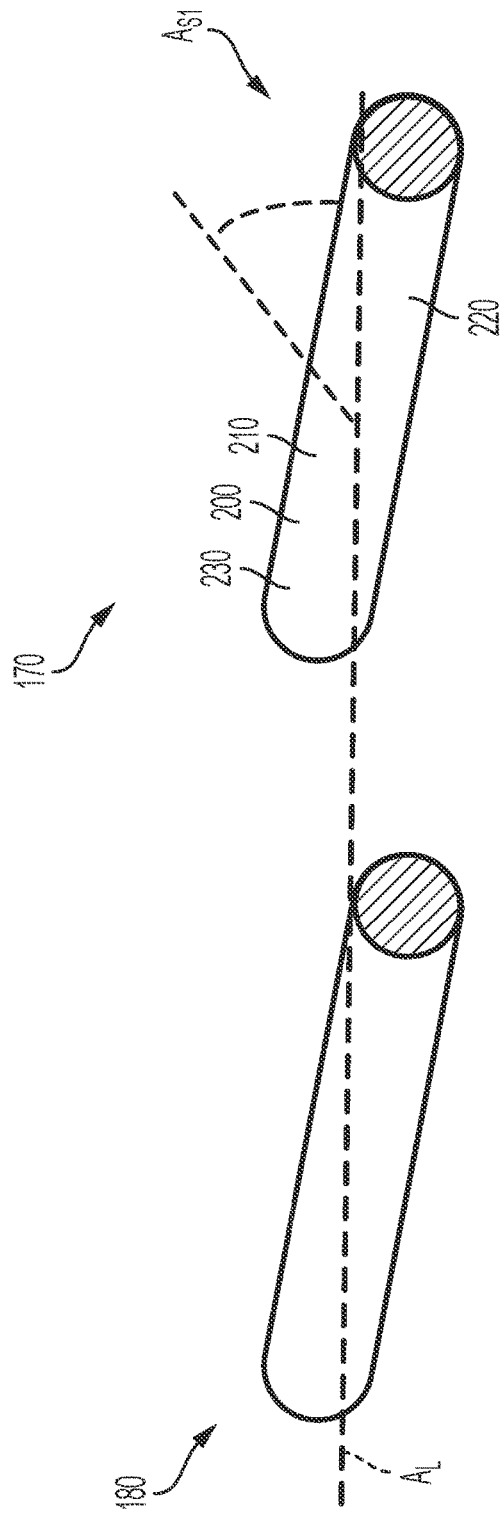
FIG. 6A shows a transverse cross-section of the frame of FIG. 5 in an expanded configuration, according to some embodiments.
Figure 6B:
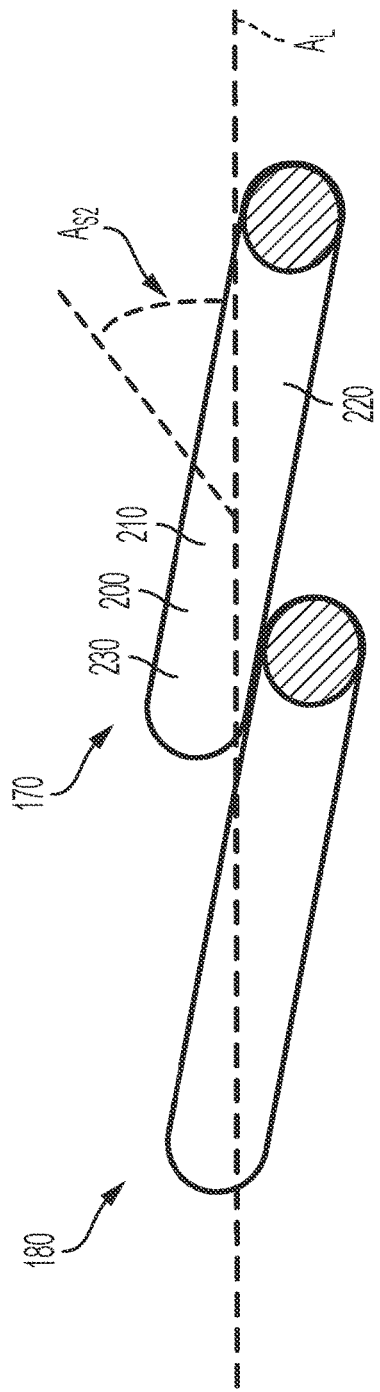
FIG. 6B shows a transverse cross-section of the frame of FIG. 5 in a compressed configuration, according to some embodiments.

FIGS. 6A and 6B show a transverse cross-section of the frame 100 along line 6-6 of FIG. 5. FIG. 6A shows the frame 100 in the expanded configuration and FIG. 6B shows the frame 100 in the collapsed configuration. FIG. 6A shows the first series of peaks 200 of both first row 170 and second row 180, and in particular the first and second legs 220 and 230 extending from the apices 210 while the stent 100 is in an expanded or deployed configuration.

In some embodiments, each of the first series of peaks 200 is angled radially outward at the first splay angle $A_{S1}$ while the second series of peaks 300 are not angled radially outward, such that the first series of peaks 200 of one circumferential row are configured to nest over the second series of peaks 300 of an adjacent circumferential row. In other words, the first series of peaks 200 are radially offset with respect to the second series of peaks 300. For example, where each of the first row 170 and second row 180 include a first series of peaks 200 and a second series of peaks 300, the first series of peaks 200 of row 170 do not overlap the second series of peaks 300 of the row 180 when the frame 100 is in the expanded configuration, and the first series of peaks 200 of row 170 overlap or nest over the second series of peaks 300 of row 180 when the frame 100 is in the compressed configuration. For reference, the terms "nest" and/or "nesting" may refer to longitudinal overlapping of adjacent rows 160 of the frame member 140. As discussed above, such nesting may promote a more even distribution of stress and strain along the frame 100, or may facilitate compacting of the frame 100 into a smaller, compressed profile. For example, in certain instances, radial and/or longitudinal compression of the frame 100 can cause the first apex angle $A_1$ to decrease and the first splay angle to increase. Thus, initially angling the first series of peaks 200 radially outward at the first splay angle $A_{S1}$ may promote nesting when this compression occurs.

FIG. 6B shows the frame 100 in the compressed configuration, according to some embodiments. In some embodiments, the first splay angle $A_{S1}$ may slightly increase upon compression of the frame 100 and nesting of adjacent rows. For example, FIG. 6B illustrates the nesting and the overlap of the first row 170 and the second row 180. In some embodiments, the first splay angle $A_{S1}$ may remain substantially the same while the frame 100 transitions from the expanded state to the compressed state and vice versa. For example, the first splay angle $A_{S1}$ may remain within about 5% of its value between the expanded state and the compressed state.

As discussed above, in some embodiments, the first series of peaks 200 are angled or raised an amount equal to the diameter of one frame element 140 to promote nesting over adjacent rows 160 of frame elements 140. The first series of peaks 200 and/or the apices 210 may be raised radially, for example, by wrapping each row 160 of the frame member 140 around a mandrel having circumferentially oriented lengths of wire W disposed thereon, as shown in FIG. 5. In some embodiments, the wire W may have a diameter equal to that of the frame member 140. As shown, each portion of the row 160 overlying the wire W will be raised by approximately the diameter of the wire W, as discussed above.

Figure 7:
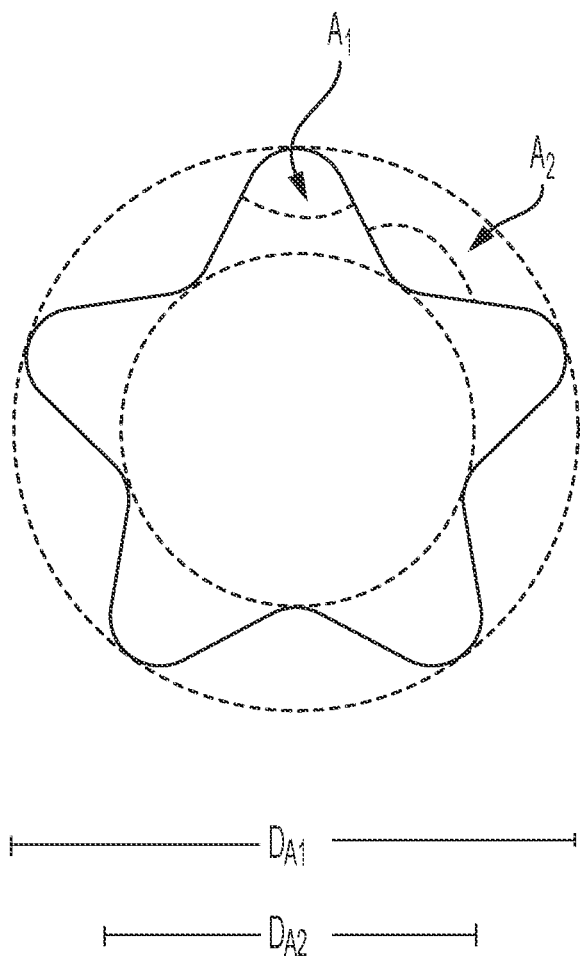
FIG. 7 is an end view of the implantable medical device of FIG. 5 in an expanded configuration and FIG. 7A is an end view of the implantable medical device of FIG. 5 in a compressed configuration, according to some embodiments.

FIG. 7 is an end view of the implantable medical device of FIG. 5, according to some embodiments and illustrating the implantable medical device in an expanded configuration. As shown, the first series of peaks 200 has an average first peak deployed diameter $D_{A1}$ that is greater than the average deployed diameter $D_{S1}$ of the frame 100. For example, the average first peak deployed diameter $D_{A1}$ of the first series of peaks 200 may be from about 2 percent to 5 percent larger than the average deployed diameter $D_{S1}$ of the frame 100. In various embodiments, the average first peak deployed diameter $D_{A1}$ of the first series of peaks 200 is greater than the average second peak deployed diameter $D_{A2}$ of the second series of peaks 300 when the second series of peaks 300 are not raised radially outward. In some embodiments, the average second peak deployed diameter $D_{A2}$ is less than the average deployed diameter $D_{S1}$ of the frame 100.

Figure 7A:
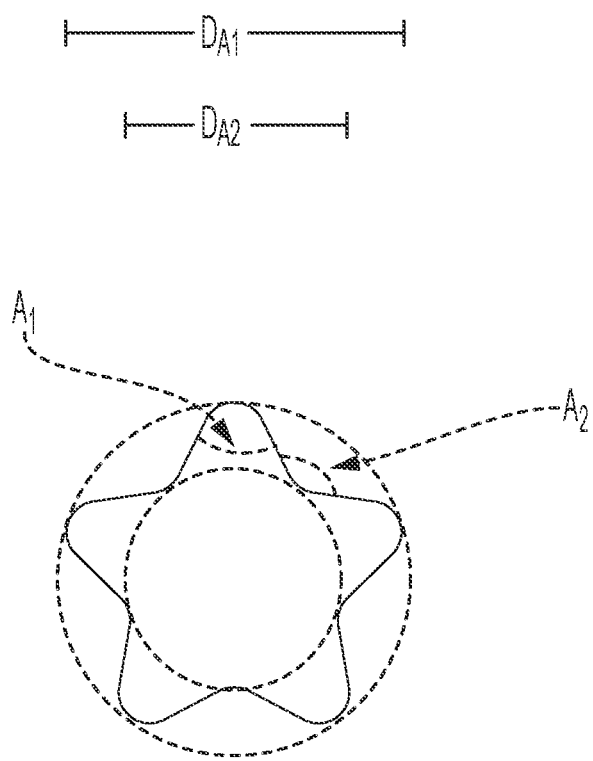

In some embodiments, when the frame 100 is in the compressed configuration, the first apex angle $A_1$ may be greater than the second apex angle $A_2$. In other words, the average apex angle of the first series of peaks 200 may be greater than the average apex angle of the second series of peaks 300. In some embodiments, a ratio of the first average apex angle $A_1$ to the second average apex angle $A_2$ may be about three-to-one. In other examples, the first average apex angle $A_1$ may be greater than the second average apex angle $A_2$. However, the first and second apex angles $A_1$ and $A_2$ can be any combination of angles as desired and may depend on a variety of factors including delivery and/or deployed lengths and diameters of the frame 100, the configuration of the frame 100 and/or frame elements 140, among other things. For example, FIG. 7A illustrates a schematic end view of the implantable medical device in a compressed configuration. As illustrated, in the compressed configuration the average first peak deployed diameter $D_{A1}$ is greater than the average deployed diameter $D_{S1}$ of the frame 100.

The device shown in FIGS. 6A-B is provided as an example of the various features of the device and, although the combination of those illustrated features is clearly within the scope of invention, that example and its illustration is not meant to suggest the inventive concepts provided herein are limited from fewer features, additional features, or alternative features to one or more of those features shown in FIGS. 6A-B. For example, in various embodiments, the longitudinally-splayed features of the frame 100 shown in FIGS. 6A-B may include the circumferentially-canted features described with reference to FIGS. 3A-B. It should also be understood that the reverse is true as well. One or more of the features depicted in FIGS. 3A-B can be employed in addition to, or as an alternative to features depicted in FIG. 6A-B. For example, the circumferentially-canted features shown in FIGS. 3A-B may be employed in connection with the longitudinally-splayed features of the frame 100 shown in FIGS. 6A-B. In other words, the first series of peaks 200 and/or the second series of peaks 300 of the frame 100 may be canted, splayed, or both canted and splayed, as desired.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A medical device having an expanded configuration and a collapsed configuration, the medical device comprising:
   a frame having a central longitudinal axis extending in a longitudinal direction, a first end, a second end, a lumen extending between the first end and the second end, and a length, the frame including an undulating frame element along its length, the undulating frame element including a first series of peaks oriented toward the first end and a second series of peaks oriented toward the second end,
   wherein each of the first series of peaks is circumferentially canted at a first cant angle in the expanded configuration and in the collapsed configuration, the first cant angle having a nonzero value, and
   wherein the first cant angle is equivalent in the compressed configuration and in the expanded configuration.

2. The medical device of claim 1, wherein each of the first series of peaks is angled radially outward relative to the central longitudinal axis at a first longitudinal splay angle.

3. The medical device of claim 1, wherein the first series of peaks are radially offset relative to the second series of peaks.

4. The medical device of claim 1, wherein the frame defines a first diameter corresponding to the first series of peaks and the frame defines a second diameter corresponding to the second series of peaks, the second diameter being less than the first diameter.

5. The medical device of claim 4, wherein the second diameter is less than the first diameter when the frame is in the expanded configuration and when the frame is in the collapsed configuration.

6. The medical device of claim 1, wherein the frame includes a first circumferential row defining the first and second series of peaks and a second circumferential row including a first series of peaks and a second series of peaks, wherein the first series of peaks of the first row overlap with the second series of peaks of the second row when the frame is in the collapsed configuration and the first series of peaks of the first row are non-overlapping with the second series of peaks of the second row when the frame is in the expanded configuration.

7. A medical device having an expanded configuration and a collapsed configuration, the medical device comprising:
   a frame having a central longitudinal axis, a circumferential direction that is transverse to the central longitudinal axis, a first end, a second end, a lumen extending between the first end and the second end, and a length, the frame including a serpentine frame element along its length, the serpentine frame element including a first series of peaks oriented toward the first end and a second series of peaks oriented toward the second end,
   wherein each of the first series of peaks is circumferentially canted at a first cant angle when the medical device is in the expanded configuration and in the collapsed configuration, the first cant angle having a nonzero value, and wherein a value of the first cant angle in the collapsed configuration is the same as a value of the first cant angle in the expanded configuration.

8. The medical device of claim 7, wherein each of the second series of peaks is circumferentially canted at a second cant angle, and wherein the second cant angle has a nonzero value.

9. The medical device of claim 8, wherein the first cant angle is equal to the second cant angle.

10. The medical device of claim 7, wherein the frame includes a first circumferential row defining the first and second series of peaks and a second circumferential row including a first series of peaks and a second series of peaks, wherein the first series of peaks of the first row overlap with the second series of peaks of the second row when the frame is in the collapsed configuration and the first series of peaks of the first row are non-overlapping with the second series of peaks of the second row when the frame is in the expanded configuration.

11. The medical device of claim 10, wherein the second series of peaks of the first row and the second series of peaks of the second row are circumferentially canted at a second cant angle such that the first series of peaks of the first row shingle adjacent portions of the second series of peaks of the second row in the collapsed configuration.

12. A medical device having an expanded configuration and a collapsed configuration, the medical device comprising:
a frame having a central longitudinal axis, a circumferential direction that is transverse to the central longitudinal axis, a first end, a second end, a lumen extending between the first end and the second end, and a length, the frame including an undulating frame element along its length, the undulating frame element including a first series of peaks oriented toward the first end and a second series of peaks oriented toward the second end,
wherein each of the first series of peaks is longitudinally splayed radially outward at a first splay angle; and
wherein each of the peaks of the first series of peaks is circumferentially canted at a first cant angle when the medical device is in the expanded configuration and in the collapsed configuration, the first cant angle having a nonzero value, and
wherein the first cant angle is equivalent in the compressed configuration and in the expanded configuration.

13. The medical device of claim 12, wherein the frame includes a first circumferential row defining the first and second series of peaks and a second circumferential row including a first series of peaks and a second series of peaks, wherein the first series of peaks of the first row overlap with the second series of peaks of the second row when the frame is in the collapsed configuration and the first series of peaks of the first row are non-overlapping with the second series of peaks of the second row when the frame is in the expanded configuration.

14. The medical device of claim 13, wherein the first splay angle remains within 15% of its value between the collapsed configuration and the expanded configuration.

* * * * *